United States Patent
Fowler et al.

(10) Patent No.: US 9,566,054 B2
(45) Date of Patent: Feb. 14, 2017

(54) FOAM INTRODUCTION SYSTEM INCLUDING MODIFIED PORT GEOMETRY

(71) Applicant: Covidien LP, Mansfield, MA (US)

(72) Inventors: David N. Fowler, Cheshire, CT (US); David Farascioni, Bethel, CT (US); Daniel Galel, Palo Alto, CA (US)

(73) Assignee: Covidien LP, Mansfield, MA (US)

( * ) Notice: Subject to any disclaimer, the term of this patent is extended or adjusted under 35 U.S.C. 154(b) by 286 days.

(21) Appl. No.: 14/310,068

(22) Filed: Jun. 20, 2014

(65) Prior Publication Data

US 2014/0303445 A1    Oct. 9, 2014

Related U.S. Application Data

(60) Continuation of application No. 13/913,552, filed on Jun. 10, 2013, now Pat. No. 8,795,289, which is a division of application No. 12/939,204, filed on Nov. 4, 2010, now Pat. No. 8,480,683.

(60) Provisional application No. 61/263,927, filed on Nov. 24, 2009.

(51) Int. Cl.
| | | |
|---|---|---|
| *A61F 11/00* | (2006.01) | |
| *A61B 17/02* | (2006.01) | |
| *A61B 17/34* | (2006.01) | |

(52) U.S. Cl.
CPC ....... *A61B 17/0218* (2013.01); *A61B 17/3423* (2013.01); *A61B 2017/348* (2013.01); *A61B 2017/3429* (2013.01); *A61B 2017/3445* (2013.01); *A61B 2017/3488* (2013.01)

(58) Field of Classification Search
CPC ............ A61B 17/0218; A61B 17/3423; A61B 2017/3429; A61B 2017/3445; A61B 2017/348; A61B 2017/3488
See application file for complete search history.

(56) References Cited

U.S. PATENT DOCUMENTS

| | | | |
|---|---|---|---|
| 4,016,884 | A | 4/1977 | Kwan-Gett |
| 4,112,932 | A | 9/1978 | Chiulli |
| 4,183,357 | A | 1/1980 | Bentley et al. |
| 4,402,683 | A | 9/1983 | Kopman |

(Continued)

FOREIGN PATENT DOCUMENTS

| | | |
|---|---|---|
| EP | 0807416 A2 | 11/1997 |
| EP | 0950376 A1 | 10/1999 |

(Continued)

OTHER PUBLICATIONS

First Examination Report EP10251983.2 issued in Europe dated Nov. 27, 2015.

(Continued)

*Primary Examiner* — Ashley Fishback

(57) ABSTRACT

A surgical apparatus for positioning within a tissue tract accessing an underlying body cavity includes a seal anchor member including leading portion, a trailing portion, and an intermediate portion disposed between the leading and trailing portions. The leading portion of the seal anchor member is configured and adapted to ease insertion of the seal anchor member into the tissue tract. Subsequent to insertion of the seal anchor member, the leading portion of the seal anchor member is also configured and adapted to facilitate securing and/or anchoring of the seal anchor member within the tissue tract.

20 Claims, 12 Drawing Sheets

(56) References Cited

U.S. PATENT DOCUMENTS

| | | |
|---|---|---|
| 4,653,476 A | 3/1987 | Bonnet |
| 4,863,430 A | 9/1989 | Klyce et al. |
| 4,863,438 A | 9/1989 | Gauderer et al. |
| 5,073,169 A | 12/1991 | Raiken |
| 5,082,005 A | 1/1992 | Kaldany |
| 5,159,921 A | 11/1992 | Hoover |
| 5,176,697 A | 1/1993 | Hasson et al. |
| 5,183,471 A | 2/1993 | Wilk |
| 5,192,301 A | 3/1993 | Kamiya et al. |
| 5,242,409 A | 9/1993 | Buelna |
| 5,242,415 A | 9/1993 | Kantrowitz et al. |
| 5,257,973 A | 11/1993 | Villasuso |
| 5,257,975 A | 11/1993 | Foshee |
| 5,269,772 A | 12/1993 | Wilk |
| 5,312,391 A | 5/1994 | Wilk |
| 5,330,486 A | 7/1994 | Wilk |
| 5,334,143 A | 8/1994 | Carroll |
| 5,345,927 A | 9/1994 | Bonutti |
| 5,366,478 A | 11/1994 | Brinkerhoff et al. |
| 5,375,588 A | 12/1994 | Yoon |
| 5,391,156 A | 2/1995 | Hildwein et al. |
| 5,395,367 A | 3/1995 | Wilk |
| 5,437,683 A | 8/1995 | Neumann et al. |
| 5,460,170 A | 10/1995 | Hammerslag |
| 5,480,410 A | 1/1996 | Cuschieri et al. |
| 5,490,843 A | 2/1996 | Hildwein et al. |
| 5,507,758 A | 4/1996 | Thomason et al. |
| 5,511,564 A | 4/1996 | Wilk |
| 5,514,133 A | 5/1996 | Golub et al. |
| 5,514,153 A | 5/1996 | Bonutti |
| 5,522,791 A | 6/1996 | Leyva |
| 5,524,644 A | 6/1996 | Crook |
| 5,540,648 A | 7/1996 | Yoon |
| 5,545,179 A | 8/1996 | Williamson, IV |
| 5,601,581 A | 2/1997 | Fogarty et al. |
| 5,634,911 A | 6/1997 | Hermann et al. |
| 5,634,937 A | 6/1997 | Mollenauer et al. |
| 5,649,550 A | 7/1997 | Crook |
| 5,651,771 A | 7/1997 | Tangherlini et al. |
| 5,653,705 A | 8/1997 | de la Torre et al. |
| 5,672,168 A | 9/1997 | de la Torre et al. |
| 5,683,378 A | 11/1997 | Christy |
| 5,685,857 A | 11/1997 | Negus et al. |
| 5,713,858 A | 2/1998 | Heruth et al. |
| 5,713,869 A | 2/1998 | Morejon |
| 5,728,103 A | 3/1998 | Picha et al. |
| 5,730,748 A | 3/1998 | Fogarty et al. |
| 5,735,791 A | 4/1998 | Alexander, Jr. et al. |
| 5,741,298 A | 4/1998 | MacLeod |
| 5,782,817 A | 7/1998 | Franzel et al. |
| 5,795,290 A | 8/1998 | Bridges |
| 5,803,921 A | 9/1998 | Bonadio |
| 5,810,712 A | 9/1998 | Dunn |
| 5,813,409 A | 9/1998 | Leahy et al. |
| 5,830,191 A | 11/1998 | Hildwein et al. |
| 5,836,871 A | 11/1998 | Wallace et al. |
| 5,842,971 A | 12/1998 | Yoon |
| 5,848,992 A | 12/1998 | Hart et al. |
| 5,853,417 A | 12/1998 | Fogarty et al. |
| 5,857,461 A | 1/1999 | Levitsky et al. |
| 5,865,817 A | 2/1999 | Moenning et al. |
| 5,871,474 A | 2/1999 | Hermann et al. |
| 5,876,413 A | 3/1999 | Fogarty et al. |
| 5,894,843 A | 4/1999 | Benetti et al. |
| 5,899,208 A | 5/1999 | Bonadio |
| 5,899,913 A | 5/1999 | Fogarty et al. |
| 5,904,703 A | 5/1999 | Gilson |
| 5,906,577 A | 5/1999 | Beane et al. |
| 5,916,198 A | 6/1999 | Dillow |
| 5,941,898 A | 8/1999 | Moenning et al. |
| 5,951,588 A | 9/1999 | Moenning |
| 5,957,913 A | 9/1999 | de la Torre et al. |
| 5,964,781 A | 10/1999 | Mollenauer et al. |
| 5,976,174 A | 11/1999 | Ruiz |
| 5,997,515 A | 12/1999 | de la Torre et al. |
| 6,017,355 A | 1/2000 | Hessel et al. |
| 6,018,094 A | 1/2000 | Fox |
| 6,024,736 A | 2/2000 | de la Torre et al. |
| 6,033,426 A | 3/2000 | Kaji |
| 6,033,428 A | 3/2000 | Sardella |
| 6,042,573 A | 3/2000 | Lucey |
| 6,048,309 A | 4/2000 | Flom et al. |
| 6,059,816 A | 5/2000 | Moenning |
| 6,068,639 A | 5/2000 | Fogarty et al. |
| 6,077,288 A | 6/2000 | Shimomura et al. |
| 6,086,603 A | 7/2000 | Termin et al. |
| 6,099,506 A | 8/2000 | Macoviak et al. |
| 6,110,154 A | 8/2000 | Shimomura et al. |
| 6,142,936 A | 11/2000 | Beane et al. |
| 6,171,282 B1 | 1/2001 | Ragsdale |
| 6,197,002 B1 | 3/2001 | Peterson |
| 6,217,555 B1 | 4/2001 | Hart et al. |
| 6,228,063 B1 | 5/2001 | Aboul-Hosn |
| 6,238,373 B1 | 5/2001 | de la Torre et al. |
| 6,241,768 B1 | 6/2001 | Agarwal et al. |
| 6,254,534 B1 | 7/2001 | Butler et al. |
| 6,264,604 B1 | 7/2001 | Kieturakis et al. |
| 6,315,770 B1 | 11/2001 | de la Torre et al. |
| 6,319,246 B1 | 11/2001 | de la Torre et al. |
| 6,371,968 B1 | 4/2002 | Kogasaka et al. |
| 6,382,211 B1 | 5/2002 | Crook |
| 6,423,036 B1 | 7/2002 | Van Huizen |
| 6,440,061 B1 | 8/2002 | Wenner et al. |
| 6,440,063 B1 | 8/2002 | Beane et al. |
| 6,443,957 B1 | 9/2002 | Addis |
| 6,447,489 B1 | 9/2002 | Peterson |
| 6,450,983 B1 | 9/2002 | Rambo |
| 6,454,783 B1 | 9/2002 | Piskun |
| 6,464,686 B1 | 10/2002 | O'Hara et al. |
| 6,468,292 B1 | 10/2002 | Mollenauer et al. |
| 6,488,620 B1 | 12/2002 | Segermark et al. |
| 6,488,692 B1 | 12/2002 | Spence et al. |
| 6,527,787 B1 | 3/2003 | Fogarty et al. |
| 6,551,270 B1 | 4/2003 | Bimbo et al. |
| 6,558,371 B2 | 5/2003 | Dorn |
| 6,578,577 B2 | 6/2003 | Bonadio et al. |
| 6,582,364 B2 | 6/2003 | Butler et al. |
| 6,589,167 B1 | 7/2003 | Shimomura et al. |
| 6,613,952 B2 | 9/2003 | Rambo |
| 6,623,426 B2 | 9/2003 | Bonadio et al. |
| 6,669,674 B1 | 12/2003 | Macoviak et al. |
| 6,676,639 B1 | 1/2004 | Ternstrom |
| 6,706,050 B1 | 3/2004 | Giannadakis |
| 6,723,044 B2 | 4/2004 | Pulford et al. |
| 6,723,088 B2 | 4/2004 | Gaskill, III et al. |
| 6,725,080 B2 | 4/2004 | Melkent et al. |
| 6,800,084 B2 | 10/2004 | Davison et al. |
| 6,814,078 B2 | 11/2004 | Crook |
| 6,837,893 B2 | 1/2005 | Miller |
| 6,840,946 B2 | 1/2005 | Fogarty et al. |
| 6,840,951 B2 | 1/2005 | de la Torre et al. |
| 6,846,287 B2 | 1/2005 | Bonadio et al. |
| 6,863,674 B2 | 3/2005 | Kasahara et al. |
| 6,878,110 B2 | 4/2005 | Yang et al. |
| 6,890,295 B2 | 5/2005 | Michels et al. |
| 6,913,609 B2 | 7/2005 | Yencho et al. |
| 6,916,310 B2 | 7/2005 | Sommerich |
| 6,916,331 B2 | 7/2005 | Mollenauer et al. |
| 6,929,637 B2 | 8/2005 | Gonzalez et al. |
| 6,939,296 B2 | 9/2005 | Ewers et al. |
| 6,945,932 B1 | 9/2005 | Caldwell et al. |
| 6,958,037 B2 | 10/2005 | Ewers et al. |
| 6,972,026 B1 | 12/2005 | Caldwell et al. |
| 6,991,602 B2 | 1/2006 | Nakazawa et al. |
| 6,997,909 B2 | 2/2006 | Goldberg |
| 7,001,397 B2 | 2/2006 | Davison et al. |
| 7,008,377 B2 | 3/2006 | Beane et al. |
| 7,014,628 B2 | 3/2006 | Bousquet |
| 7,033,319 B2 | 4/2006 | Pulford et al. |
| 7,052,454 B2 | 5/2006 | Taylor |
| 7,056,321 B2 | 6/2006 | Pagliuca et al. |
| 7,077,852 B2 | 7/2006 | Fogarty et al. |
| 7,081,089 B2 | 7/2006 | Bonadio et al. |
| 7,100,614 B2 | 9/2006 | Stevens et al. |

(56) References Cited

U.S. PATENT DOCUMENTS

| | | |
|---|---|---|
| 7,101,353 B2 | 9/2006 | Lui et al. |
| 7,104,981 B2 | 9/2006 | Elkins et al. |
| 7,153,261 B2 | 12/2006 | Wenchell |
| 7,163,510 B2 | 1/2007 | Kahle et al. |
| 7,192,436 B2 | 3/2007 | Sing et al. |
| 7,195,590 B2 | 3/2007 | Butler et al. |
| 7,214,185 B1 | 5/2007 | Rosney et al. |
| 7,217,277 B2 | 5/2007 | Parihar et al. |
| 7,223,257 B2 | 5/2007 | Shubayev et al. |
| 7,223,278 B2 | 5/2007 | Davison et al. |
| 7,235,084 B2 | 6/2007 | Skakoon et al. |
| 7,238,154 B2 | 7/2007 | Ewers et al. |
| 7,276,075 B1 | 10/2007 | Callas et al. |
| 7,294,103 B2 | 11/2007 | Bertolero et al. |
| 7,300,399 B2 | 11/2007 | Bonadio et al. |
| 7,316,699 B2 | 1/2008 | McFarlane |
| 7,331,940 B2 | 2/2008 | Sommerich |
| 7,344,547 B2 | 3/2008 | Piskun |
| 7,377,898 B2 | 5/2008 | Ewers et al. |
| 7,390,322 B2 | 6/2008 | McGuckin, Jr. et al. |
| 7,393,322 B2 | 7/2008 | Wenchell |
| 7,412,977 B2 | 8/2008 | Fields et al. |
| 7,445,597 B2 | 11/2008 | Butler et al. |
| 7,452,363 B2 | 11/2008 | Ortiz |
| 7,473,221 B2 | 1/2009 | Ewers et al. |
| 7,540,839 B2 | 6/2009 | Butler et al. |
| 7,559,893 B2 | 7/2009 | Bonadio et al. |
| 7,645,232 B2 | 1/2010 | Shluzas |
| 7,650,887 B2 | 1/2010 | Nguyen et al. |
| 7,704,207 B2 | 4/2010 | Albrecht et al. |
| 7,717,847 B2 | 5/2010 | Smith |
| 7,727,146 B2 | 6/2010 | Albrecht et al. |
| 7,736,306 B2 | 6/2010 | Brustad et al. |
| 7,798,898 B2 | 9/2010 | Luciano, Jr. et al. |
| 8,795,289 B2 | 8/2014 | Fowler et al. |
| 2001/0037053 A1 | 11/2001 | Bonadio et al. |
| 2002/0038077 A1 | 3/2002 | de la Torre et al. |
| 2002/0055714 A1 | 5/2002 | Rothschild |
| 2002/0183594 A1 | 12/2002 | Beane et al. |
| 2003/0014076 A1 | 1/2003 | Mollenauer et al. |
| 2003/0135091 A1 | 7/2003 | Nakazawa et al. |
| 2003/0236549 A1 | 12/2003 | Bonadio et al. |
| 2004/0049099 A1 | 3/2004 | Ewers et al. |
| 2004/0092795 A1 | 5/2004 | Bonadio et al. |
| 2004/0092796 A1 | 5/2004 | Butler et al. |
| 2004/0111061 A1 | 6/2004 | Curran |
| 2004/0138529 A1 | 7/2004 | Wiltshire et al. |
| 2004/0167543 A1 | 8/2004 | Mazzocchi et al. |
| 2004/0267096 A1 | 12/2004 | Caldwell et al. |
| 2005/0020884 A1 | 1/2005 | Hart et al. |
| 2005/0043592 A1 | 2/2005 | Boyd et al. |
| 2005/0070935 A1 | 3/2005 | Ortiz |
| 2005/0096695 A1 | 5/2005 | Olich |
| 2005/0148823 A1 | 7/2005 | Vaugh et al. |
| 2005/0159651 A1 | 7/2005 | Raymond et al. |
| 2005/0192483 A1 | 9/2005 | Bonadio et al. |
| 2005/0203346 A1 | 9/2005 | Bonadio et al. |
| 2005/0241647 A1 | 11/2005 | Nguyen et al. |
| 2005/0288558 A1 | 12/2005 | Ewers et al. |
| 2006/0020241 A1 | 1/2006 | Piskun et al. |
| 2006/0049317 A1 | 3/2006 | Reutenauer et al. |
| 2006/0084842 A1 | 4/2006 | Hart et al. |
| 2006/0129165 A1 | 6/2006 | Edoga et al. |
| 2006/0149137 A1 | 7/2006 | Pingleton et al. |
| 2006/0149306 A1 | 7/2006 | Hart et al. |
| 2006/0161049 A1 | 7/2006 | Beane et al. |
| 2006/0161050 A1 | 7/2006 | Butler et al. |
| 2006/0229501 A1 | 10/2006 | Jensen et al. |
| 2006/0241651 A1 | 10/2006 | Wilk |
| 2006/0247498 A1 | 11/2006 | Bonadio et al. |
| 2006/0247499 A1 | 11/2006 | Butler et al. |
| 2006/0247500 A1 | 11/2006 | Voegele et al. |
| 2006/0247516 A1 | 11/2006 | Hess et al. |
| 2006/0247586 A1 | 11/2006 | Voegele et al. |
| 2006/0247673 A1 | 11/2006 | Voegele et al. |
| 2006/0247678 A1 | 11/2006 | Weisenburgh et al. |
| 2006/0258899 A1 | 11/2006 | Gill et al. |
| 2006/0270911 A1 | 11/2006 | Voegele et al. |
| 2007/0093695 A1 | 4/2007 | Bonadio et al. |
| 2007/0118175 A1 | 5/2007 | Butler et al. |
| 2007/0149859 A1 | 6/2007 | Albrecht et al. |
| 2007/0151566 A1 | 7/2007 | Kahle et al. |
| 2007/0156023 A1 | 7/2007 | Frasier et al. |
| 2007/0185387 A1 | 8/2007 | Albrecht et al. |
| 2007/0203398 A1 | 8/2007 | Bonadio et al. |
| 2007/0208312 A1 | 9/2007 | Norton et al. |
| 2007/0255222 A1 * | 11/2007 | Li ................. A61J 15/0015 604/174 |
| 2008/0009826 A1 | 1/2008 | Miller et al. |
| 2008/0027476 A1 | 1/2008 | Piskun |
| 2008/0097162 A1 | 4/2008 | Bonadio et al. |
| 2008/0200767 A1 | 8/2008 | Ewers et al. |
| 2008/0255519 A1 | 10/2008 | Piskun et al. |
| 2009/0012477 A1 | 1/2009 | Norton et al. |
| 2009/0093752 A1 | 4/2009 | Richard et al. |
| 2009/0137879 A1 | 5/2009 | Ewers et al. |
| 2009/0182279 A1 | 7/2009 | Wenchell et al. |
| 2009/0187079 A1 | 7/2009 | Albrecht et al. |
| 2009/0326330 A1 | 12/2009 | Bonadio et al. |
| 2009/0326332 A1 | 12/2009 | Carter |
| 2009/0326461 A1 | 12/2009 | Gresham |
| 2010/0249523 A1 | 9/2010 | Spiegal et al. |

FOREIGN PATENT DOCUMENTS

| | | |
|---|---|---|
| EP | 1312318 A1 | 5/2003 |
| EP | 1774918 A1 | 4/2007 |
| EP | 2044889 A1 | 4/2009 |
| EP | 2044897 A1 | 4/2009 |
| WO | 93/14801 | 8/1993 |
| WO | 94/04067 | 3/1994 |
| WO | 96/36283 | 11/1996 |
| WO | 97/33520 | 9/1997 |
| WO | 97/42889 | 11/1997 |
| WO | 99/16368 | 4/1999 |
| WO | 00/32120 | 6/2000 |
| WO | 01/49363 | 7/2001 |
| WO | 02/07611 | 1/2002 |
| WO | 2006/100658 A2 | 9/2006 |
| WO | 2008/015566 A2 | 2/2008 |
| WO | 2008/042005 | 4/2008 |
| WO | 2008/093313 | 8/2008 |
| WO | 2008/121294 A1 | 10/2008 |

OTHER PUBLICATIONS

European Search Report for corresponding to EP 10251983, dated Feb. 15, 2011 (3 pages).
Canadian Office Action issued in corresponding Canadian Application No. 2,720,545 dated Jul. 26, 2016.

* cited by examiner

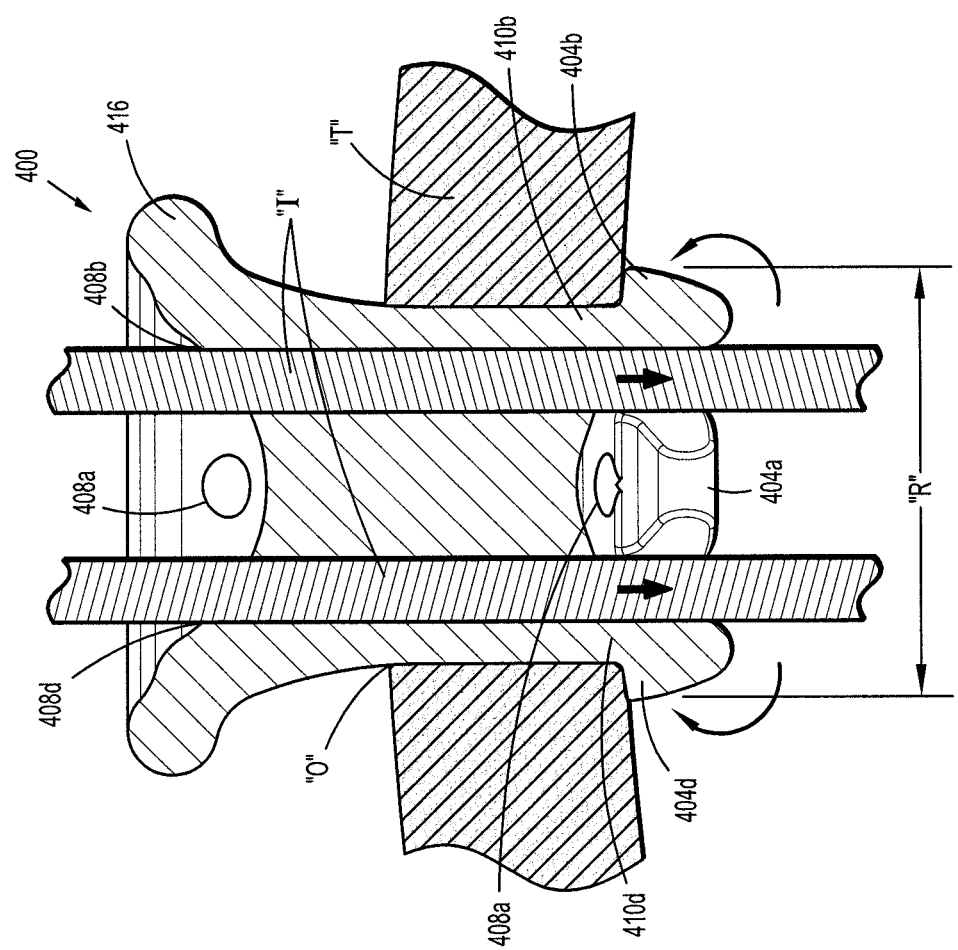

FOAM INTRODUCTION SYSTEM INCLUDING MODIFIED PORT GEOMETRY

CROSS-REFERENCE TO RELATED APPLICATIONS

This application is a continuation of U.S. patent application Ser. No. 13/913,552 filed Jun. 10, 2013, now U.S. Pat. No. 8,795,289, which is a divisional of U.S. patent application Ser. No. 12/939,204 filed Nov. 4, 2010, now U.S. Pat No. 8,480,683, which claims benefit of U.S. Provisional Application No. 61/263,927 filed Nov 24, 2009, and the disclosures of each of the above-identified applications are hereby incorporated by reference in their entirety.

BACKGROUND

Technical Field

The present disclosure relates generally to a seal for use in a surgical procedure. More particularly, the present disclosure relates to a seal anchor member adapted for insertion into an incision, or a naturally occurring bodily orifice, in tissue, and, for the sealed reception of one or more surgical objects such that a substantially fluid-tight seal is formed with both the tissue and the surgical object or objects.

Background of Related Art

A minimally invasive surgical procedure is one in which a surgeon enters a patient's body through a small opening in the skin or through a naturally occurring opening (e.g., mouth, anus, or vagina). Such procedures have several advantages over traditional open surgeries. In particular, as compared to traditional open surgeries, minimally invasive surgical procedures result in reduced trauma and recovery time for patients. Generally, such procedures are referred to as "endoscopic", unless performed on the patient's abdomen, in which case the procedure is referred to as "laparoscopic". Throughout the present disclosure, the term "minimally invasive" should be understood to encompass both endoscopic and laparoscopic procedures.

During a typical minimally invasive procedure, surgical objects, such as surgical access devices (e.g., trocar and cannula assemblies) or endoscopes, are inserted into the patient's body through the incision in tissue. In general, prior to the introduction of the surgical object into the patient's body, insufflation gases are used to enlarge the area surrounding the target surgical site to create a larger, more accessible work area. Accordingly, the maintenance of a substantially fluid-tight seal is desirable so as to prevent the escape of the insufflation gases and the deflation or collapse of the enlarged surgical site.

To this end, various valves and seals are used during the course of minimally invasive procedures and are widely known in the art. However, a continuing need exists for a seal anchor member that can be inserted directly into the incision in tissue and that can accommodate a variety of surgical objects while maintaining the integrity of an insufflated workspace.

SUMMARY

Disclosed herein is a surgical apparatus for positioning within a tissue tract accessing an underlying body cavity. The surgical apparatus includes a seal anchor member including a leading portion, a trailing portion, and an intermediate portion disposed between the leading and trailing portions. One or more lumens longitudinally extend between the leading and trailing portions. The one or more lumens are configured and adapted to receive instrumentation therein in a substantially sealed relation.

The leading portion of the seal anchor member is transitionable between a first configuration and a second configuration. The arrangement and/or interrelationship between the elements, e.g., the elements of the leading portion of the seal anchor member may be different in the first and second configurations. For example, the positioning of elements with respect to each other may differ in the first and second configurations. The leading portion may define a radial dimension, diameter or a width that corresponds to each of the first and second configurations. In an embodiment, the leading portion includes a plurality of positioning members defining at least one gap between adjacent positioning members to facilitate compression of the leading portion in a transverse direction. The at least one gap facilitates transitioning the leading portion to the second configuration in which the leading portion has a substantially flat profile, thereby facilitating insertion of the seal anchor member within the tissue tract.

In another embodiment, the leading portion of the seal anchor member may include one or more positioning segments that are radially coupled to the intermediate portion of the seal anchor member, e.g., the one or more positioning members are operably connected to the intermediate portion. To facilitate insertion of the seal anchor member within the tissue member the one or more positioning members are inwardly directed to minimize the size of the leading portion of the seal anchor member. Once inserted into the tissue tract, the one or more positioning members may deploy outwardly, thereby increasing the size of the leading portion of the seal anchor member and facilitating stabilization and/or anchoring of the seal anchor member within the tissue tract. The one or more positioning members may be biased inwardly, and may deflect outwardly in response to insertion of instrumentation through the lumens of the seal anchor member.

In yet another embodiment, a seal anchor member may include a leading portion, a trailing portion, and an intermediate portion disposed therebetween. A first positioning member may be associated with the trailing portion, and a second positioning member may be associated with the leading portion. The second positioning member may have a non-circular, e.g., an oblong shape or configuration. The non-circular shape of the second positioning member facilitates insertion by guiding the seal anchor member to a proper position within the tissue tract. Once positioned within the tissue tract, the non-circular shape of the second positioning member also facilitates anchoring and/or securing of the seal anchor member within the tissue tract. The seal anchor member may also include one or more longitudinally extending lumens between the leading and trailing portions of the seal anchor member.

These and other features of the apparatus disclosed herein will become more readily apparent to those skilled in the art from the following detailed description of various embodiments of the present disclosure.

BRIEF DESCRIPTION OF THE DRAWINGS

Various embodiments of the present disclosure are described hereinbelow with reference to the drawings, wherein:

FIG. 16 is a side cross-sectional view of the seal anchor member of FIG. 8 as shown in FIG. 15 in a second condition.

DETAILED DESCRIPTION OF EMBODIMENTS

Figure 1:
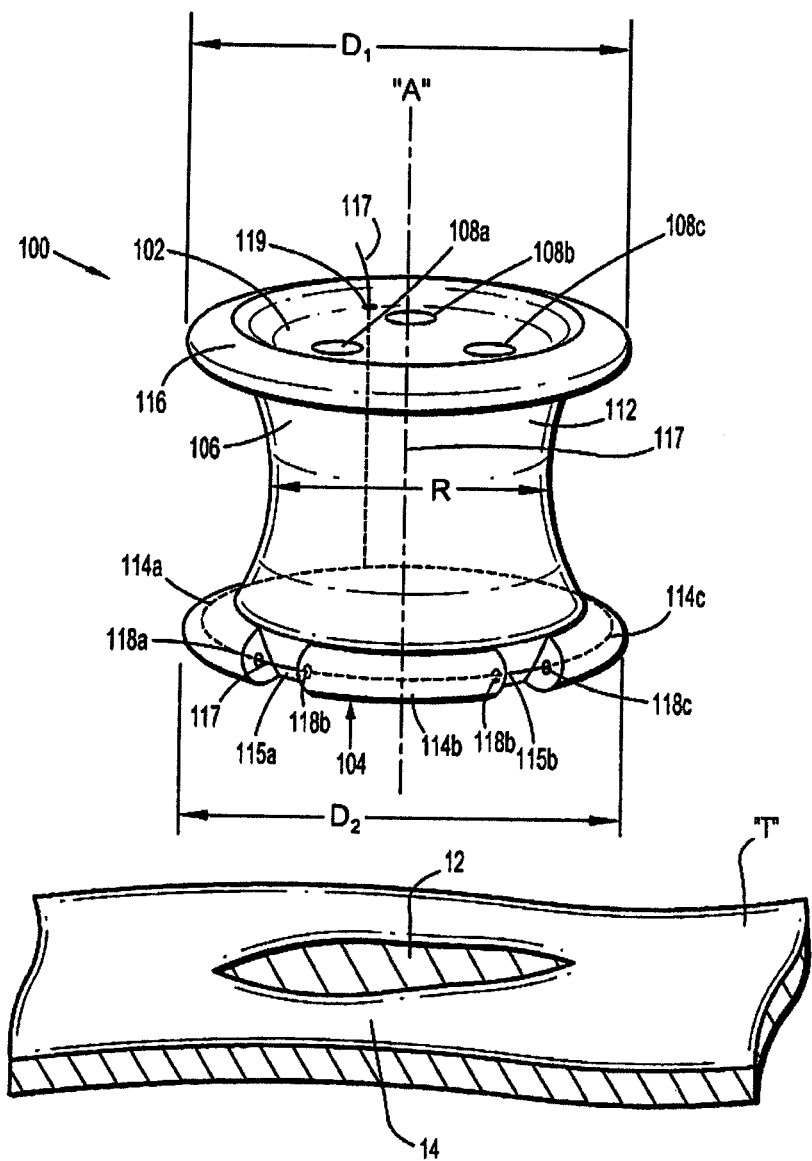
FIG. 1 is a perspective view of a seal anchor member in accordance with the principles of the present disclosure shown in a first condition positioned relative to tissue.

In the figures and in the description that follows, in which like reference numerals identify similar or identical elements, the term "proximal" will refer to the end of the apparatus that is closest to the clinician during use, while the term "distal" will refer to the end that is farthest from the clinician, as is traditional and known in the art.

Figure 2:
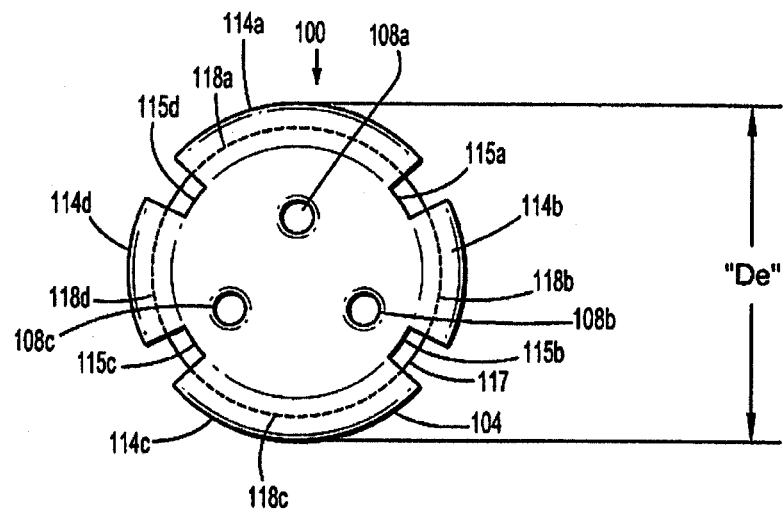
FIG. 2 is a bottom view of the seal anchor member of FIG. 1.
Figure 3:
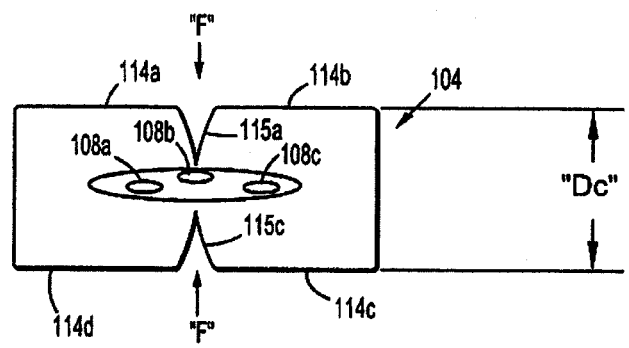
FIG. 3 is a bottom view of the seal anchor member of FIG. 1 shown in a second condition.

With reference to FIGS. 1-3, a seal anchor member 100 will now be described. Seal anchor member 100 includes a body 112 defining a longitudinal axis "A" and having respective trailing (proximal) and leading (distal) portions 102, 104, and an intermediate section 106 disposed between the trailing and leading portions 102, 104. Seal anchor member 100 includes one or more ports 108a, 108b, 108c that extend generally longitudinally between trailing and leading portions 102, 104, respectively, and through seal anchor member 100.

Associated with trailing and leading portions 102, 104 are positioning members 116 and 114a-d, respectively. Positioning members 116, 114a-d may be composed of any suitable material that is at least semi-resilient to facilitate resilient deformation of the positioning members 116, 114a-d. The positioning members 116, 114a-d may exhibit any suitable configuration and may be, for example, substantially annular-shaped or oval-shaped arrangement. As shown in FIG. 2, a diameter of the leading portion 104, when in its initial, expanded, condition, has dimension "De".

As shown best in FIG. 2, associated with the leading portion 104 are positioning members 114a-d that are separated by surfaces 115a-d that define gaps among positioning members 114a-d. While four positioning members 114a-d are depicted in FIGS. 1-3, a greater or lesser number of positioning members, configured to define gaps therebetween, may be utilized to achieve a desired configuration of the seal anchor member 100 when compressed.

Figure 3A:
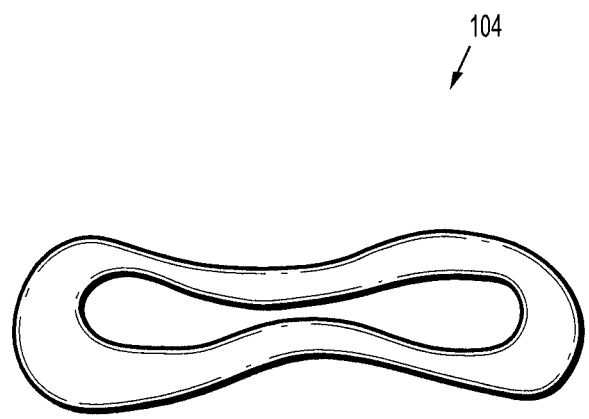
FIG. 3A is a bottom view of a seal anchor member having a single annular positioning member.

For insertion of seal anchor member 100 within a tissue tract 12, positioning members 114a-d are brought in closer proximity to one another to facilitate placement of the seal anchor member 100 within the tissue tract. The separation between the positioning members 114a-d facilitates transition of the distal portion 104 between a substantially annular profile (FIG. 2) to a substantially rectangular profile (FIG. 3). The gaps between the positioning members 114a-d help facilitate the transition of leading portion 104 to a substantially flatter profile, such that distal portion 104 has a dimension "Dc", as shown in FIG. 3, upon application of a force "F" than may have been achievable in the absence of such gaps. In particular, if the distal portion 104 included only a single annular positioning member, compression of the distal end 104 would result in a non-uniform contour (FIG. 3A) of the seal anchor member 100, e.g., the seal anchor member 100 would be compressed more greatly, e.g., would be flatter, at the point of the application of the force and less greatly farther away from that point.

Subsequent to insertion of the seal anchor member 100 within the tissue tract, the resilient nature of the positioning members 114a-d, 116 allows the positioning members to expand to approximate the tissue tract 12 when seal anchor member 100 is inserted. Positioning members 114a-d, 116 may engage walls defining the body cavity to further facilitate securement of seal anchor member 100 within the body tissue "T". For example, positioning members 114a-d at leading portion 104 may engage the internal peritoneal wall and positioning member 116 adjacent trailing portion 102 may engage the outer epidermal tissue adjacent the incision 12 within tissue "T".

The use and function of seal anchor member 100 during the course of a typical minimally invasive procedure will now be discussed. Initially, an incision is made through the tissue. Such an incision is typically made with a scalpel or the like, resulting in a generally slit-shaped opening. Next, a body cavity, e.g., the peritoneal cavity, is insufflated with a suitable biocompatible gas such as, e.g., carbon dioxide, such that the cavity wall is raised and lifted away from the internal organs and tissue housed therein, providing greater access thereto. Insufflation of the body cavity may be performed with an insufflation needle or similar device, as is conventional in the art.

The seal anchor member 100 is in an expanded state at rest, as shown in FIG. 2. Insertion of the seal anchor member 100 within the tissue tract 12 is achievable by compressing the leading portion 104 of the seal anchor member 100. Positioning member 114 is adapted and configured to become substantially flat (when viewed from below) upon the application of a force "F" as seen in FIG. 3. Compression of the seal anchor member 100 facilitates insertion of the seal anchor member 100 into the tissue tract 12. Subsequent to the insertion of the seal anchor member 100, leading portion 104, positioning members 114a-d and at least a section 112 of intermediate portion 106 are disposed beneath tissue "T". Seal anchor member 100 is caused to transition from the compressed state as shown in FIG. 3 towards the expanded state (FIG. 1) by removing force "F" therefrom. Expansion of the section 112 of the intermediate portion 106 is limited by the tissue surfaces 14 (FIG. 1) defining tissue tract 12, thereby subjecting intermediate portion 106 to an external force "F" that is directed inwardly. The internal biasing force of seal anchor member 100 is outwardly directed and is exerted upon tissue surfaces 14 upon insertion of the seal anchor member 100 within tissue tract 12, thereby facilitating a substantially fluid-tight seal between the seal anchor member 100 and tissue surfaces 14 and substantially preventing the escape of insufflation gas around seal anchor member 100 and through tissue tract 12.

In the expanded condition, the respective radial dimensions $D_1$, $D_2$ of the trailing and leading portions 102, 104 are substantially larger than the radial dimension R of the intermediate portion 106 thereby giving seal anchor member 100 an "hour-glass" configuration. Subsequent to insertion, the radial dimension $D_2$ of distal portion 104 increases to provide an interference fit with the tissue tract 12. Consequently, seal anchor member 100 resists removal from tissue tract 12 when in the expanded condition and thus, seal anchor member 100 will remain anchored within the tissue "T" until it is returned to its compressed condition and is pulled out of the tissue tract 12.

Optionally, as shown in FIGS. 1-2, each of the positioning members 114a-d at the distal portion 104 of the seal anchor member 100 may include a lumen 118a, 118b, 118c, 118d, respectively. Lumens 118a-d are configured and adapted to receive a drawstring 117 therein. Seal anchor member 100 may further include a longitudinally extending lumen 119 adapted for reception of the drawstring 117. During a procedure, the surgeon may move the drawstring 117 through lumen 119 by pulling the drawstring 117 in a proximal direction thereby reducing the length of the drawstring 117 positioned within lumens 118a-d. Moving the drawstring 117 through lumen 119 forces the positioning members 114a-d to move toward one another thereby reducing the gaps defined among the positioning members 114a-d.

During a surgical procedure, the surgeon places the seal anchor member 100 relative to the tissue tract 12 of the tissue "T", as shown in FIG. 1. As discussed above, the size of the distal portion (leading portion) 104 is reduced by proximally pulling the drawstring 117. Once the distal portion 104 is sufficiently compressed (FIG. 3), the surgeon inserts the distal portion 104 into the tissue tract 12. With the distal portion 104 compressed, the seal anchor member 100 may taper from the proximal (trailing) to the distal (lead) portions of the seal anchor member 100. Both the reduced cross-section of the distal portion 104 and the resulting taper of the seal anchor member 100 facilitate the surgeon's insertion of the seal anchor member 100 into the tissue tract 12.

The internal bias of the seal anchor member 100 will apply a force to transition the distal portion 104 back to its initial dimension "De". Therefore, during insertion of the seal anchor member, the surgeon may continue to pull drawstring 117 proximally to maintain the compressed dimension "Dc" of the distal portion 104. The material of the seal anchor member 100, e.g., a foam, may also facilitate a timed transition back to the initial shape and dimension of the seal anchor member 100, thereby reducing the need to apply tension to the drawstring 117 during insertion. In an embodiment, a clip or another locking means may be employed to secure the drawstring 117 in a given position, thereby maintaining a given dimension of the distal portion 104 by inhibiting the translation of the drawstring 117 through the lumen 119.

Once the surgeon has placed the seal anchor member 100 within the tissue tract 12 as desired, the surgeon will permit the drawstring 117 to translate. The internal biasing force of the seal anchor member 100 will begin to transition the distal portion 104 to the expanded dimension "De". In the expanded state, the shape and configuration of the seal anchor member 100 facilitates anchoring of the seal anchor member 100 within the tissue tract 12. Once the seal anchor member 100 is anchored within the tissue tract 12, surgical instruments are inserted through lumens 108a-c.

Upon completion of the procedure, the instruments are removed, and the drawstring 117 is once again translated proximally through lumen 119 to reduce the dimension of the distal portion 104 toward the compressed dimension "Dc". Thereafter, the surgeon removes the seal anchor member 100 from the tissue tract 12. The reduced dimension of the distal portion 104 facilitates withdrawal of the seal anchor member 100 from within the tissue tract 12 of tissue "T". The tissue tract 12 may then be closed through means known in the art, e.g., stapling or suturing.

Figure 4:
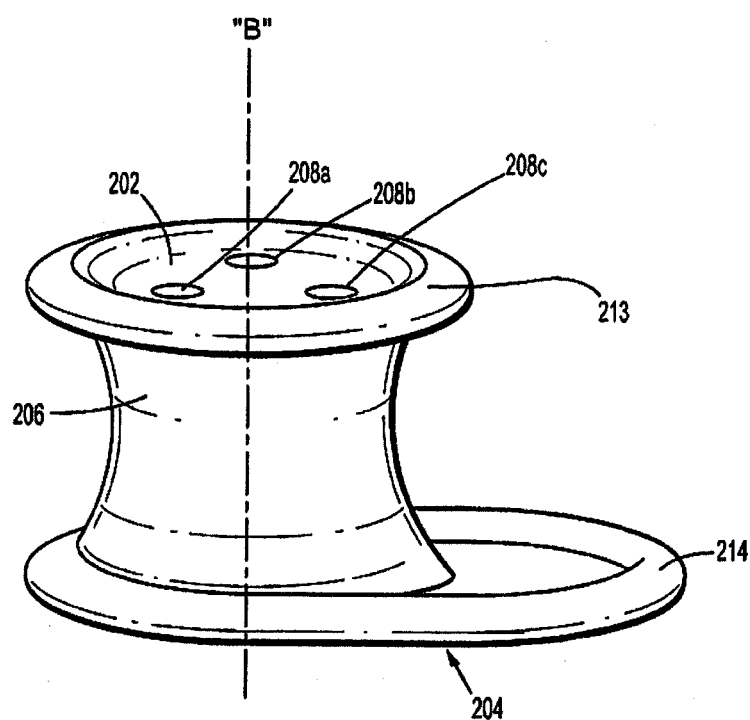
FIG. 4 is a perspective view of another embodiment of a seal anchor member in accordance with the principles of the present disclosure shown in a first condition.
Figure 5:
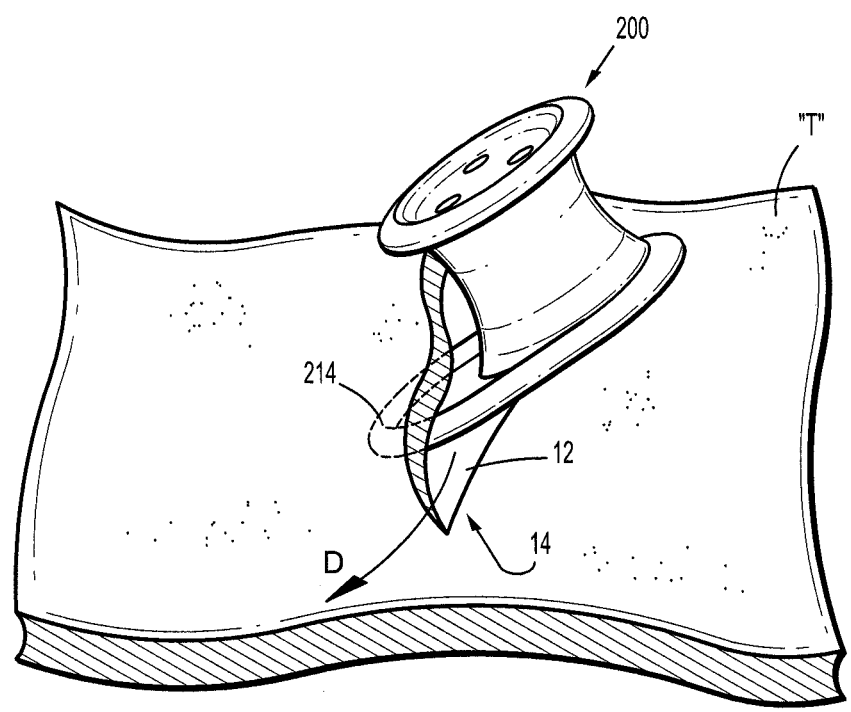
FIG. 5 is a perspective view of the seal anchor member of FIG. 4 shown partially inserted within tissue.

In another embodiment of the present disclosure, a seal anchor member 200 will now be described with reference to FIGS. 4 and 5. As shown best in FIG. 4, the seal anchor member 200 defines a longitudinal axis "B" and having respective trailing (or proximal) and leading (or distal) portions 202, 204 and an intermediate portion 206 disposed between the trailing and leading portions 202, 204. Seal anchor member 200 includes one or more ports 208a, 208b, 208c that extend longitudinally between trailing and leading portions 202, 204, respectively, and through seal anchor member 200. Positioning members 213, 214 are respectively associated with trailing portion 202 and leading portion 204.

Positioning member 214 has a non-circular, in this case, oblong shape. In an embodiment as shown in FIG. 4, the positioning member 214 has an oblong shape. The oblong shape of the positioning member 214 facilitates insertion of the seal anchor member 200 into the tissue tract 12. Distal portion 214a of positioning member 214 is configured to guide the seal anchor member 200 into the tissue tract 12.

Placement of the seal anchor member 200 within the tissue tract 12 will now be described with reference to FIG. 5. As seen in FIG. 5, introduction of the seal anchor member 200 is achieved by placing distal portion 214a within the tissue tract and translating the seal anchor port 200 along directional arrow "D" to place leading portion 204 within tissue tract 12. Surgical instruments may be used to grasp and position the leading portion 204 of the seal anchor member 200. Alternatively, a surgeon may select to grasp and position the leading portion 204 of the seal anchor member 200 with his or her hand. Upon placement of the seal anchor member 200 within the tissue tract 12, the surgeon may place instruments within the lumens 208a-c.

Upon completion of the procedure, the seal anchor member 200 is removed from within the tissue tract 12. The seal anchor member 200 may be removed by translating the seal anchor member along a path opposite that defined by directional arrow "D". In addition, the seal anchor member 200 may be formed from a compressible material. Where the seal anchor member 200 is formed from a compressible material, the surgeon may reduce the dimensions of the seal anchor member 200 by squeezing the seal anchor member 200. The reduction in the dimensions of the seal anchor member 200 may also facilitate the removal of the seal anchor member 200 from within the tissue tract 12. The tissue tract 12 may then be closed through means known in the art, e.g., stapling or suturing.

Figure 6A:
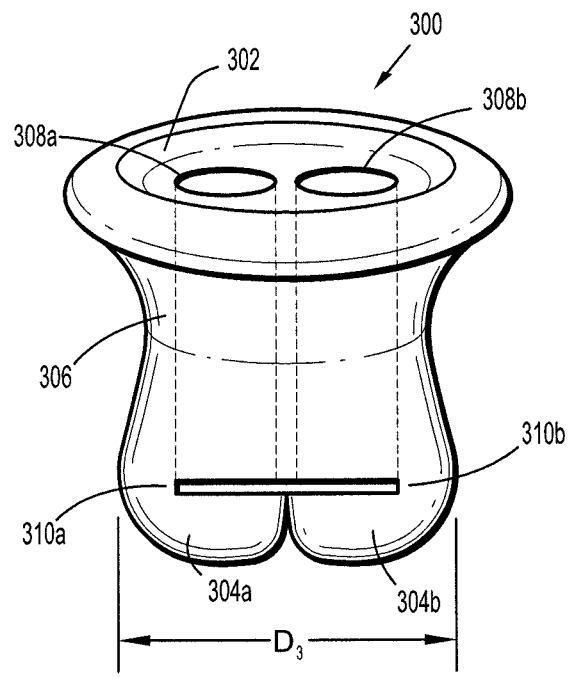
FIG. 6A is a perspective view of yet another embodiment of a seal anchor member in accordance with the principles of the present disclosure shown in a first condition.
Figure 6B:
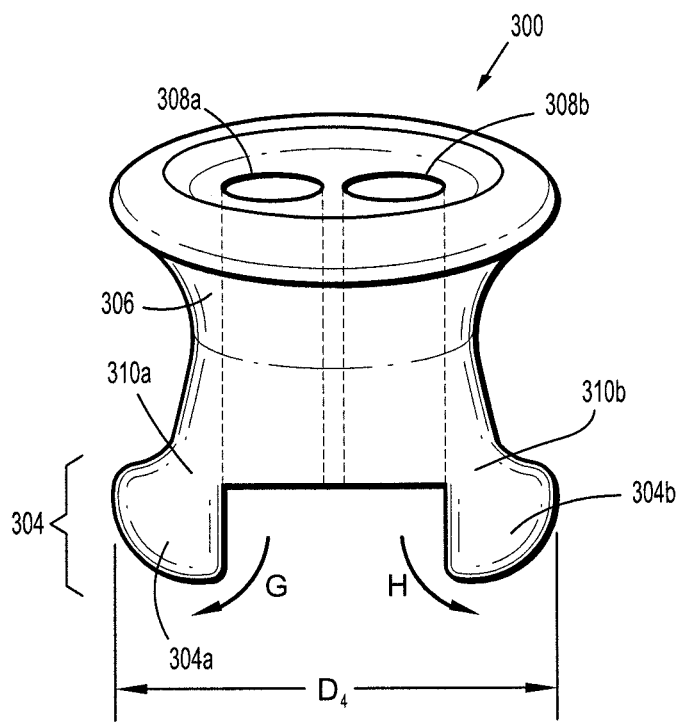
FIG. 6B is a perspective view of the seal anchor member of FIG. 6A shown in a second condition.

With reference to FIGS. 6A-6B, a seal anchor member 300 will now be described. The seal anchor member 300 includes a trailing (proximal) portion 302, a leading (distal) portion 304, and an intermediate section 306 disposed between the trailing and leading portions 302, 304. The seal anchor member 300 includes one or more longitudinally extending lumens 308a, 308b. Each of the lumens 308a-b is configured and adapted to receive a surgical instrument "I" (FIG. 7B) therethrough in a substantially sealed relationship.

The leading portion 304 includes one or more positioning segments 304a, 304b. The positioning segments 304a, 304b are operably connected to the intermediate section 306 by a living hinge 310a, 310b, respectively. While the positioning segments 304a-b are shown as being operably connected to the intermediate section 306 by a living hinge, other types of hinges may be used to facilitate the pivotal relationship between the intermediate section 306 and the positioning segments 304a-b. As shown in FIG. 6A, the seal anchor member 300 is in a first, collapsed position in which positioning segments 304a, 304b are inwardly retracted such that the leading portion 304 defines a first diameter $D_3$. In the second, expanded position (FIG. 6B), the positioning segments 304a, 304b have been deployed radially outward as indicated by directional arrows G, H, respectively. While in the second position, the leading portion 304 defines a second diameter $D_4$ that is greater than the first diameter $D_3$. Transitioning of the seal anchor member 300 between the first and second positions necessitates application of a force sufficient to radially translate the positioning segments 304a, 304b.

Figure 7A:
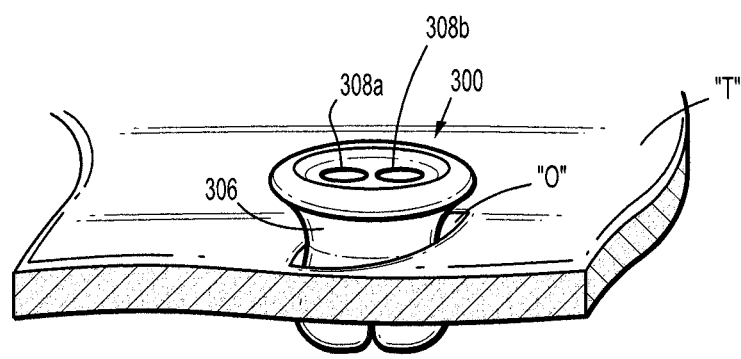
FIG. 7A is perspective view of the seal anchor member of FIG. 6A, shown placed within a wound within a tissue, while in the first condition.
Figure 7B:
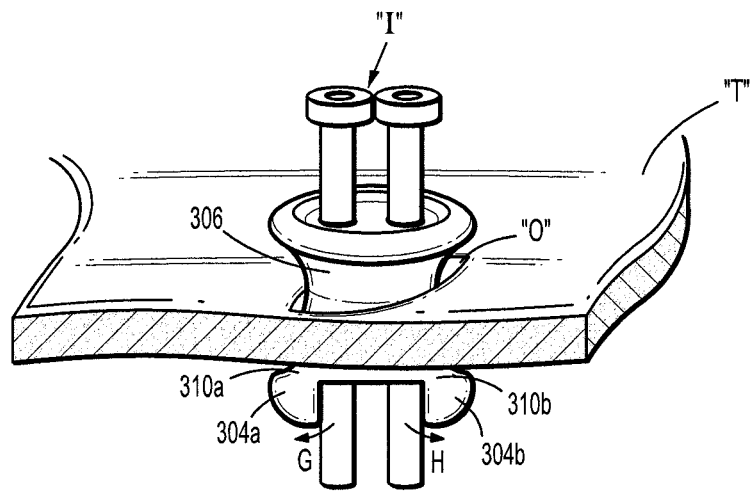
FIG. 7B is a perspective view of the seal anchor member of FIG. 6A, shown placed within a wound within a tissue, while in the second condition.
Figure 8:
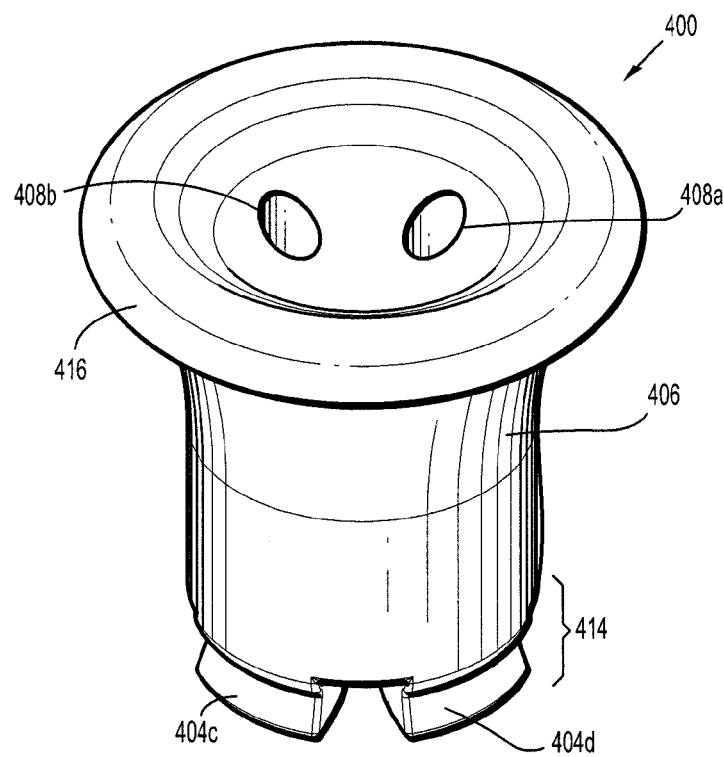
FIG. 8 is a top perspective view of yet another embodiment of a seal anchor member in accordance with the present disclosure.
Figure 9:
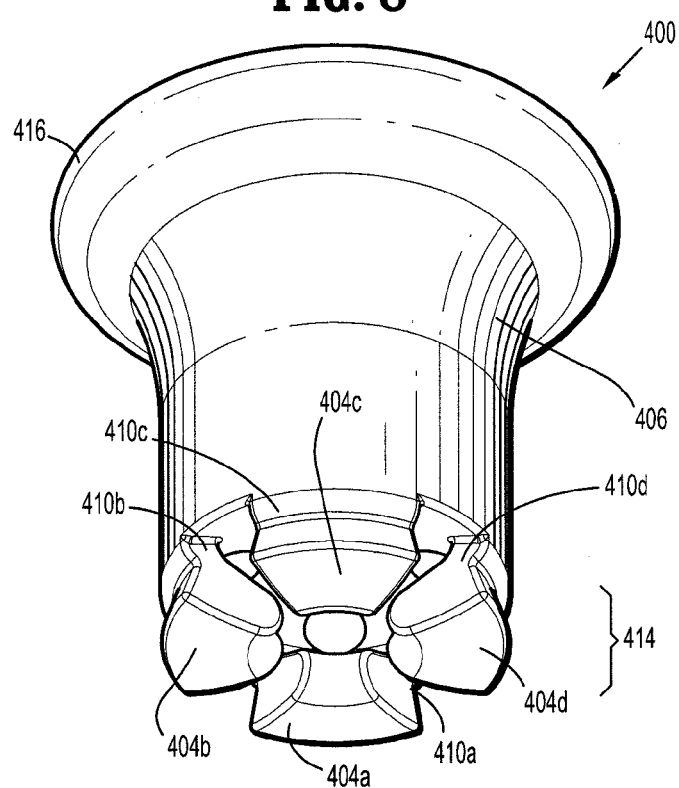
FIG. 9 is a bottom perspective view of the seal anchor member of FIG. 8.
Figure 10:
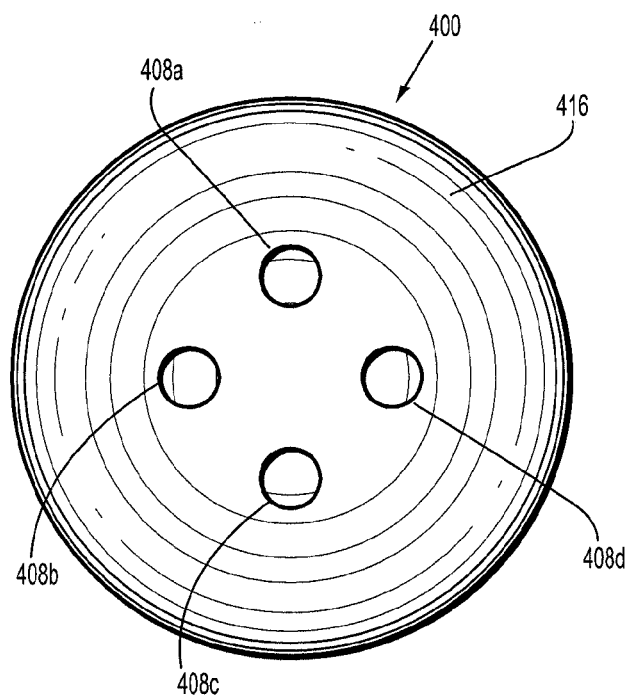
FIG. 10 is a top view of the seal anchor member of FIG. 8.
Figure 11:
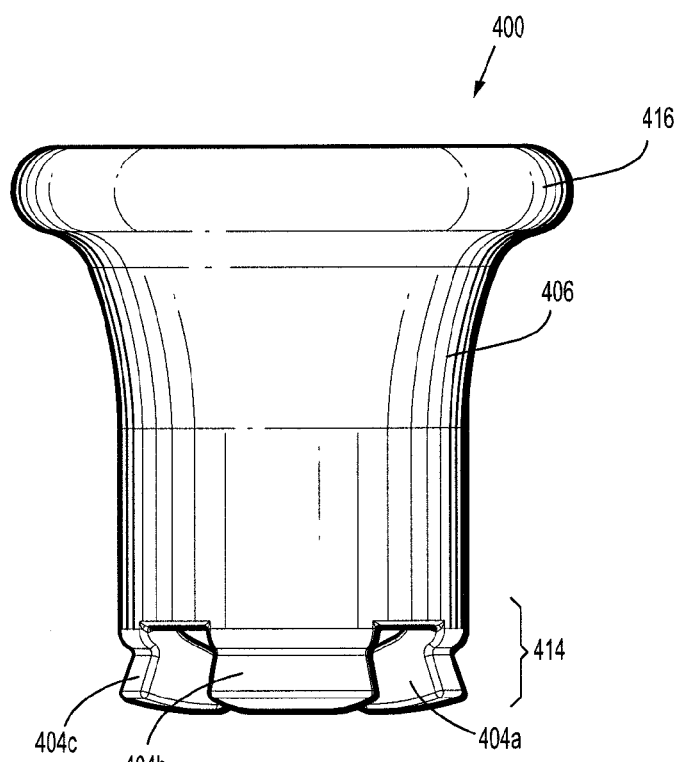
FIG. 11 is a side view of the seal anchor member of FIG. 8.
Figure 12:
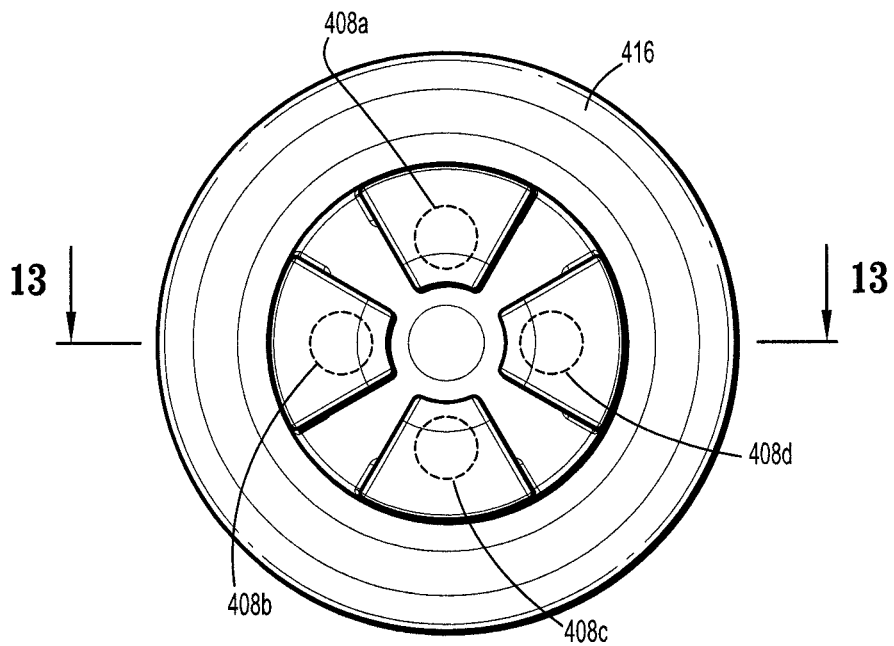
FIG. 12 is a top, partially cut-away view of the seal anchor member of FIG. 8.
Figure 13:
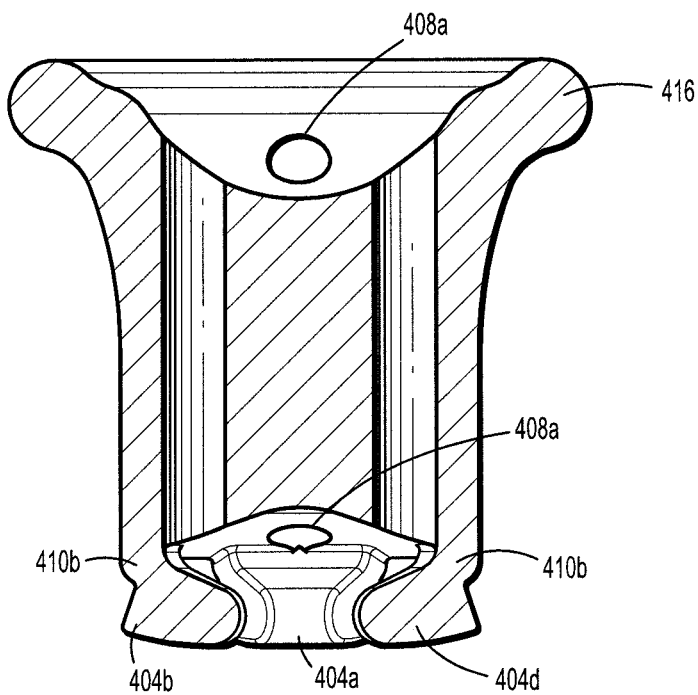
FIG. 13 is a side cross-sectional view of the seal anchor member of FIG. 8 taken along section-line 13 as shown in FIG. 12.

As shown in FIG. 7A, when the seal anchor member 300 is in the first, collapsed position, placement of the seal anchor member 300 within opening "O" of the tissue "T" is facilitated by having a comparatively smaller diameter. In addition, the comparatively smaller diameter may reduce the overall size of the opening "O" necessary to place the seal anchor member 300 within the opening "O". As shown in FIG. 7B, insertion of surgical instruments "I" through the lumen 308a, 308b effects deployment of a corresponding positioning segment 304a, 304b. In particular, insertion of surgical instrument "I" through lumen 308a effects a radial translation of positioning segment 304a in the direction indicated by arrow G. Similarly, insertion of surgical instrument "I" through lumen 308b effects a radial translation of positioning segment 304b in the direction indicated by directional arrow H.

With the positioning segments 304a, 304b deployed, the seal anchor member 300 is anchored within the opening "O" of the tissue "T". In particular, while the positioning segments 304a, 304b are in the deployed condition, the interaction of the positioning segments 304a, 304b with the tissue "T" inhibits the removal of the seal anchor member 300 from the opening "O". In particular, when the leading portion 304 is in the second position, the diameter $D_4$ is greater than the opening of opening "O", thereby inhibiting removal of the seal anchor member 300.

With the positioning segments 304a, 304b retracted, the seal anchor member 300 is inserted into the opening "O". Thereafter, the instruments "I" are inserted into lumens 308a, 308b. The insertion of the instruments "I" into lumens 308a, 308b effects a corresponding deployment of the positioning segments 304a, 304b in the direction indicated by arrows G, H, respectively. Upon completion of the surgical procedure, the seal anchor member 300 is removed from the opening "O" as will now be described. Each of the instruments "I" is removed from the lumen 308a, 308b into which it was placed. The removal of the instruments "I" effects retraction of the positioning segments 304a, 304b since the positioning segments 304a, 304b are biased inwardly. The retraction of the positioning segments 304a, 304b facilitates removal of the seal anchor member 300 by reducing the dimension of the leading portion 304 of the seal anchor member 300, i.e., distal portion 304 has a diameter $D_3$ that is less than the opening of the opening "O". Thereafter, the surgeon proximally translates the seal anchor member out of the opening "O". The opening "O" may then be closed through means known in the art, e.g., stapling or suturing.

With reference to FIGS. 8-16, a seal anchor member 400 will now be described. The seal anchor member 400 includes a trailing or a proximal portion 416, a leading or distal portion 414, and an intermediate section 406 disposed therebetween. The seal anchor member 400 includes one or more longitudinally extending lumens 408-d. Each lumen 408a-d is configured and adapted to receive a surgical instrument "I" (FIGS. 14-16) therethrough in a substantially sealed relationship. As shown best in FIG. 9, the leading portion 414 includes four positioning segments 404a-d. Although the leading portion 414 is illustrated and described herein as including four positioning segments 404a-d, the leading portion 414 may include a fewer or greater number of positioning segments, e.g., three positioning segments. Each positioning segment 404a-d is operably connected to the intermediate section 406 by a living hinge 410a-d, respectively. Although the positioning segments 404a-d are shown as being operably connected to the intermediate section 406 by a living hinge 410a-d, other types of hinges may be used to facilitate the pivotal relationship between the intermediate section 406 and the positioning segments 404a-d.

Figure 15:
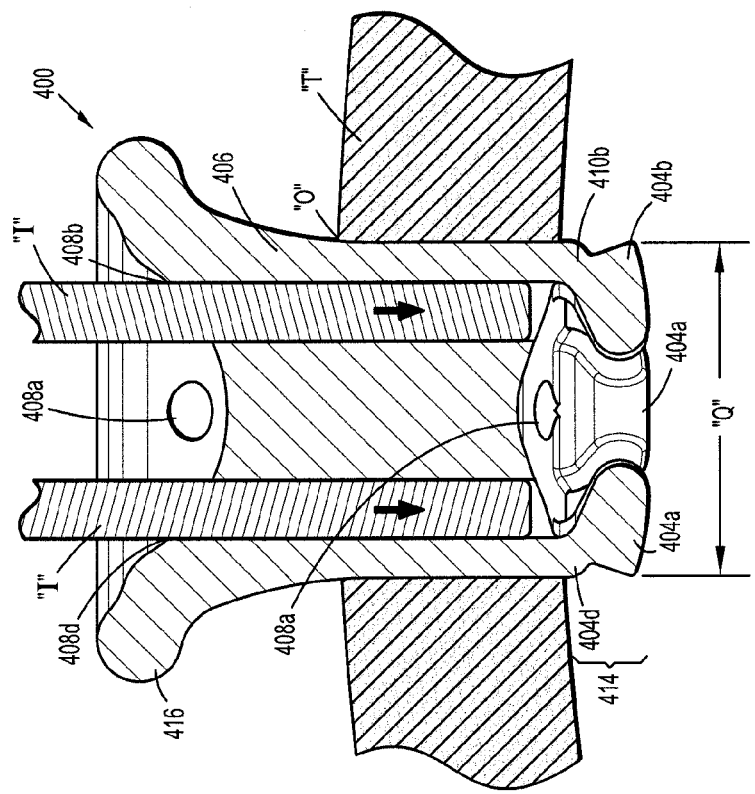
FIG. 15 is a side cross-sectional view, taken along section-line 15-15, of the seal anchor member of FIG. 8 as shown in FIG. 14.

The positioning segments 404a-d are biased inwardly such that in the absence of a force acting upon them, the positioning segments 404a-d are retracted. While the positioning segments 404a-d are in the retracted position, the leading portion 414 is in a first position and defines a first dimension "Q" to facilitate insertion of the seal anchor member 400 into an opening "O" within a tissue "T" (FIG. 15). Insertion of instrumentation "I" into the lumens 408a-d, effects deployment of respective positioning members adjacent the lumens 408a-d through which the instrumentation "I" is inserted (FIG. 16). While the positioning segments 404a-d are in the deployed position, the leading portion 414 is in a second position and defines a dimension "R", which facilitates anchoring of the seal anchor member 400 within the opening "O". In particular, when the leading portion 414 is in the first position (FIG. 15), the dimension "Q" is less than the opening of opening "O", thereby facilitating insertion of the seal anchor member 400 into the opening "O". When the leading portion 414 is in the second position (FIG. 16), the dimension "R" is greater than the opening of opening "O", thereby inhibiting removal of surgical seal anchor 400.

Figure 14:
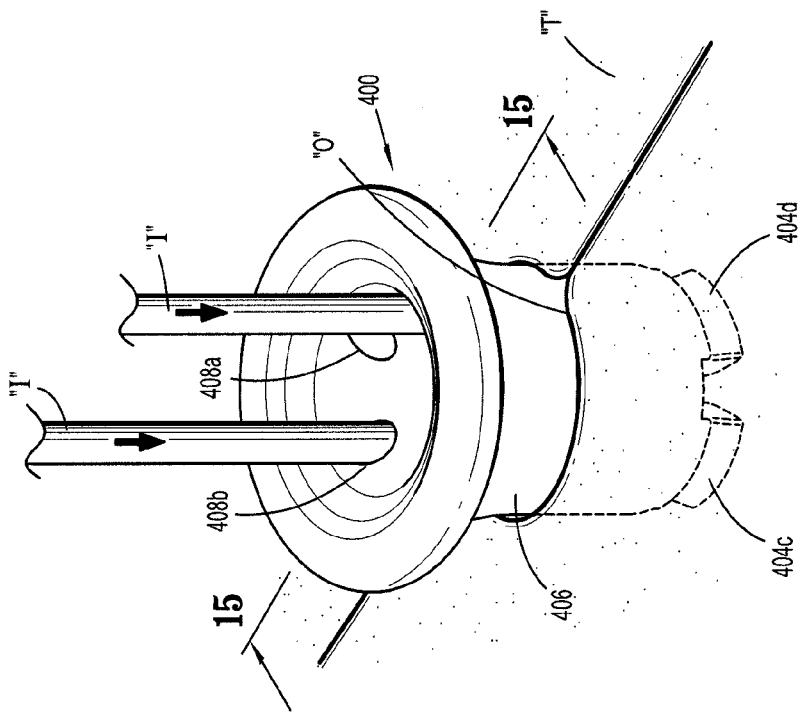
FIG. 14 is a perspective view of the seal anchor member of FIG. 8 shown placed within an incision in a first condition.

The use and operation of seal anchor member 400 will now be described with reference to FIGS. 14-16. As shown in FIG. 14, when the seal anchor member 400 is in a first, collapsed position, i.e., with positioning segments 404a-d retracted, the seal anchor member is placed within opening "O" within tissue "T". As discussed above, the positioning segments 404a-d are biased inwardly towards the refracted state such that the leading portion defines a dimension "Q" to facilitate insertion of the seal anchor member 400 into the opening "O" within tissue "T". Surgical instrumentation "I" may be partially inserted within the lumens 408a-d during the placement of the seal anchor member 400 within the opening "O" or may be inserted into the lumens 408a-d subsequent to placement of the seal anchor member 400 within the opening "O".

The distal translation of the instrumentation "I" within the lumens 408a-d will effect deployment of the positioning segments 404a-d as the instrumentation "I" comes into contact with the positioning segments 404a-d. Insertion of instrumentation "I" through a lumen 408a-d effects the deployment of a corresponding positioning member 404a-d, i.e., a positioning member 404a-d that is along the path through which the instrument "I" is translated. As shown in FIG. 16, the distal translation of the instrumentation "I" through lumens 408b, 408d, effects the radial, outward deflection of corresponding positioning segments 404b, 404d. Anchoring of the seal anchor member 400 within the opening "O" is achieved through the insertion of instruments "I" into each lumen 408a-d. However, in some situations, some of the lumens 408a-d may not have an instrument inserted therethrough. In those situations, stabilization of the seal anchor member 400 may be enhanced by inserting the instruments "I" a symmetrical pattern, i.e., pairs of instruments "I" may be inserted within lumens 408a-d that are across from one another.

Subsequent to completion of the procedure, removal of the seal anchor member 400 is facilitated by removing the instruments "I" from each lumen 408a-d. Since the positioning members 404a-d are biased toward the initial, retracted state, the leading portion 414 will transition toward smaller dimension "Q" from the greater dimension "R". This reduction in the dimension of the leading portion 414 facilitates removal of the seal anchor member 400 from within incision "I" formed within tissue "T".

Although the illustrative embodiments of the present disclosure have been described herein with reference to the accompanying drawings, the above description, disclosure, and figures should not be construed as limiting, but merely as exemplifications of particular embodiments. It is to be understood, therefore, that the disclosure is not limited to those precise embodiments, and that various other changes and modifications may be effected therein by one skilled in the art without departing from the scope or spirit of the disclosure.

The invention claimed is:

1. A surgical apparatus for positioning within a tissue tract accessing an underlying body cavity comprising:
a seal anchor member including a leading portion, a trailing portion, and an intermediate portion disposed between the leading and trailing portions, the seal anchor member formed of a foam material, the seal anchor member defining a port extending between the leading and trailing portions, the seal anchor member transitionable between an expanded state and a compressed state, the seal anchor member biased toward the expanded state; and
first and second positioning members associated with the leading portion, the first and second positioning members defining a gap therebetween.

2. The surgical apparatus according to claim 1, wherein at least one of the first and second positioning members comprises a semi-resilient material to facilitate resilient deformation thereof.

3. The surgical apparatus according to claim 1, wherein the seal anchor member is configured to be in a sealing relation with the tissue tract when positioned within the tissue tract.

4. The surgical apparatus according to claim 1, wherein the seal anchor member has an hourglass configuration when the seal anchor member is in the expanded state.

5. The surgical apparatus according to claim 1, wherein at least one of the first and second positioning members defines a lumen configured to receive a drawstring therein.

6. The surgical apparatus according to claim 5, wherein the seal anchor member further defines a longitudinal lumen configured to receive the drawstring therethrough.

7. The surgical apparatus according to claim 1, further including a drawstring associated with the first and second positioning members such that pulling of the drawstring causes the first and second positioning members to move toward each other to reduce the gap therebetween.

8. The surgical apparatus according to claim 1, further including a third positioning member associated with the trailing portion.

9. A surgical apparatus for positioning within a tissue tract accessing an underlying body cavity comprising:
a seal anchor member including a leading portion, a trailing portion, and an intermediate portion disposed between the leading and trailing portions, the seal anchor member defining a port extending between the leading and trailing portions, the seal anchor member transitionable between an expanded state and a compressed state, the seal anchor member biased toward the expanded state; and
first and second positioning members associated with the leading portion, the first and second positioning members defining a gap therebetween, wherein at least one of the first and second positioning members defines a lumen configured to receive a drawstring therein.

10. The surgical apparatus according to claim 9, wherein at least one of the first and second positioning members comprises a semi-resilient material to facilitate resilient deformation thereof.

11. The surgical apparatus according to claim 9, wherein the seal anchor member is in a sealing relation with the tissue tract when positioned within the tissue tract.

12. The surgical apparatus according to claim 9, wherein the seal anchor member has an hourglass configuration when the seal anchor member is in the expanded state.

13. The surgical apparatus according to claim 9, wherein the seal anchor member further defines a longitudinal lumen configured to receive the drawstring therethrough.

14. The surgical apparatus according to claim 9, further including a drawstring associated with the first and second positioning members such that pulling of the drawstring causes the first and second positioning members to move toward each other to reduce the gap therebetween.

15. The surgical apparatus according to claim 9, wherein the seal anchor member is formed of a foam material.

16. The surgical apparatus according to claim 9, further including a third positioning member associated with the trailing portion.

17. A surgical apparatus for positioning within a tissue tract accessing an underlying body cavity comprising:
a seal anchor member including a leading portion, a trailing portion, and an intermediate portion disposed between the leading and trailing portions, the seal anchor member defining a port extending between the leading and trailing portions, the seal anchor member transitionable between an expanded state and a compressed state, the seal anchor member biased toward the expanded state;

first and second positioning members associated with the leading portion, the first and second positioning members defining a gap therebetween; and a drawstring associated with the first and second positioning members such that pulling of the drawstring causes the first and second positioning members to move toward each other to reduce the gap therebetween.

18. The surgical apparatus according to claim 17, wherein at least one of the first and second positioning members comprises a semi-resilient material to facilitate resilient deformation thereof.

19. The surgical apparatus according to claim 17, wherein at least one of the first and second positioning members defines a lumen configured to receive the drawstring therein.

20. The surgical apparatus according to claim 19, wherein the seal anchor member further defines a longitudinal lumen configured to receive the drawstring therethrough.

* * * * *